(12) United States Patent
Bar-Tal

(10) Patent No.: US 9,414,770 B2
(45) Date of Patent: Aug. 16, 2016

(54) RESPIRATORY EFFECT REDUCTION IN CATHETER POSITION SENSING

(75) Inventor: Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 334 days.

(21) Appl. No.: 12/980,488

(22) Filed: Dec. 29, 2010

(65) Prior Publication Data

US 2012/0172712 A1 Jul. 5, 2012

(51) Int. Cl.
*A61B 5/08* (2006.01)
*A61B 17/00* (2006.01)

(52) U.S. Cl.
CPC .............. *A61B 5/0809* (2013.01); *A61B 34/20* (2016.02); *A61B 2017/00699* (2013.01); *A61B 2034/2046* (2016.02); *A61B 2034/2051* (2016.02); *A61B 2034/2053* (2016.02)

(58) Field of Classification Search
CPC .... A61B 5/0809; A61B 5/1135; A61B 7/003; A61B 5/06; A61B 19/201; A61B 19/5244; A61B 2019/5251; A61B 2017/00699; A61B 2019/5253; A61B 2019/5246
USPC .......... 600/536, 529, 534; 606/108, 433–435, 606/424, 130, 129
See application file for complete search history.

(56) References Cited

U.S. PATENT DOCUMENTS

| | | | |
|---|---|---|---|
| 5,391,199 A | 2/1995 | Ben-Haim | |
| 5,730,129 A | 3/1998 | Darrow et al. | |
| 6,298,260 B1 | 10/2001 | Sontag et al. | |
| 6,580,938 B1 | 6/2003 | Acker | |
| 6,597,939 B1 | 7/2003 | Lampotang et al. | |
| 6,711,429 B1 | 3/2004 | Gilboa et al. | |
| 7,263,397 B2 * | 8/2007 | Hauck et al. | 600/374 |
| 7,536,218 B2 | 5/2009 | Govari et al. | |
| 8,456,182 B2 | 6/2013 | Bar-Tal et al. | |
| 8,603,004 B2 * | 12/2013 | Koh et al. | 600/534 |
| 8,825,134 B2 * | 9/2014 | Danehorn | 600/424 |
| 9,023,027 B2 | 5/2015 | Bar-Tal et al. | |
| 2004/0254437 A1 | 12/2004 | Hauck et al. | |
| 2005/0107687 A1* | 5/2005 | Anderson | 600/424 |
| 2006/0241401 A1* | 10/2006 | Govari et al. | 600/424 |
| 2007/0038078 A1 | 2/2007 | Osadchy | |
| 2008/0058657 A1 | 3/2008 | Schwartz et al. | |

(Continued)

FOREIGN PATENT DOCUMENTS

| | | |
|---|---|---|
| CN | 101199416 A | 6/2008 |
| CN | 101657153 A | 2/2010 |

(Continued)

OTHER PUBLICATIONS

Extended European Search Report dated Apr. 12, 2012 from related European Application No. 11195867.4.

(Continued)

*Primary Examiner* — Michael Kahelin
*Assistant Examiner* — Tho Tran
(74) *Attorney, Agent, or Firm* — Louis J. Capezzuto

(57) ABSTRACT

A method, including positioning body-electrodes in galvanic contact with a body of a patient and locating a probe in the body of the patient. The method further includes tracking positions of the probe during respiration of the patient and determining indications related to impedances between the body-electrodes during the respiration. The method also includes calculating a function relating the positions of the probe to the indications, and applying the function to identify end-expirium points of the respiration based on subsequent indications related to the impedances.

9 Claims, 8 Drawing Sheets

(56) References Cited

U.S. PATENT DOCUMENTS

| | | | |
|---|---|---|---|
| 2008/0221459 A1* | 9/2008 | Craven et al. | 600/484 |
| 2008/0249424 A1 | 10/2008 | Harlev et al. | |
| 2009/0030307 A1 | 1/2009 | Govari et al. | |
| 2009/0182224 A1 | 7/2009 | Shmarak et al. | |
| 2009/0262979 A1 | 10/2009 | Markowitz et al. | |
| 2010/0079158 A1 | 4/2010 | Bar-Tal et al. | |
| 2011/0092809 A1* | 4/2011 | Nguyen et al. | 600/424 |
| 2011/0170625 A1 | 7/2011 | Zhang et al. | |
| 2011/0190625 A1* | 8/2011 | Harlev et al. | 600/424 |
| 2011/0190647 A1 | 8/2011 | Helfenbein et al. | |
| 2014/0221803 A1 | 8/2014 | Bar-Tal et al. | |

FOREIGN PATENT DOCUMENTS

| | | |
|---|---|---|
| JP | 2005-319256 | 11/2005 |
| JP | 2008-058657 | 3/2008 |
| JP | 2009-530047 | 8/2009 |
| JP | 2010-082446 | 4/2010 |
| WO | WO 2005/030330 A1 | 4/2005 |
| WO | WO 2007/109406 A1 | 9/2007 |
| WO | WO 2009/128062 A2 | 10/2009 |

OTHER PUBLICATIONS

Australian Examination Report, Jun. 14, 2014, from co-pending U.S. Appl. No. 12/980,488 filed on Dec. 29, 2010—pending.

Chinese Official Action and Search Report, Sep. 23, 2014, from co-pending U.S. Appl. No. 12/980,488 filed on Dec. 29, 2010—pending.

Extended European Search Report EP 11 19 5867 dated Apr. 12, 2012.

JP Office Action for JP2011-288915 dated Nov. 10, 2015.

\* cited by examiner

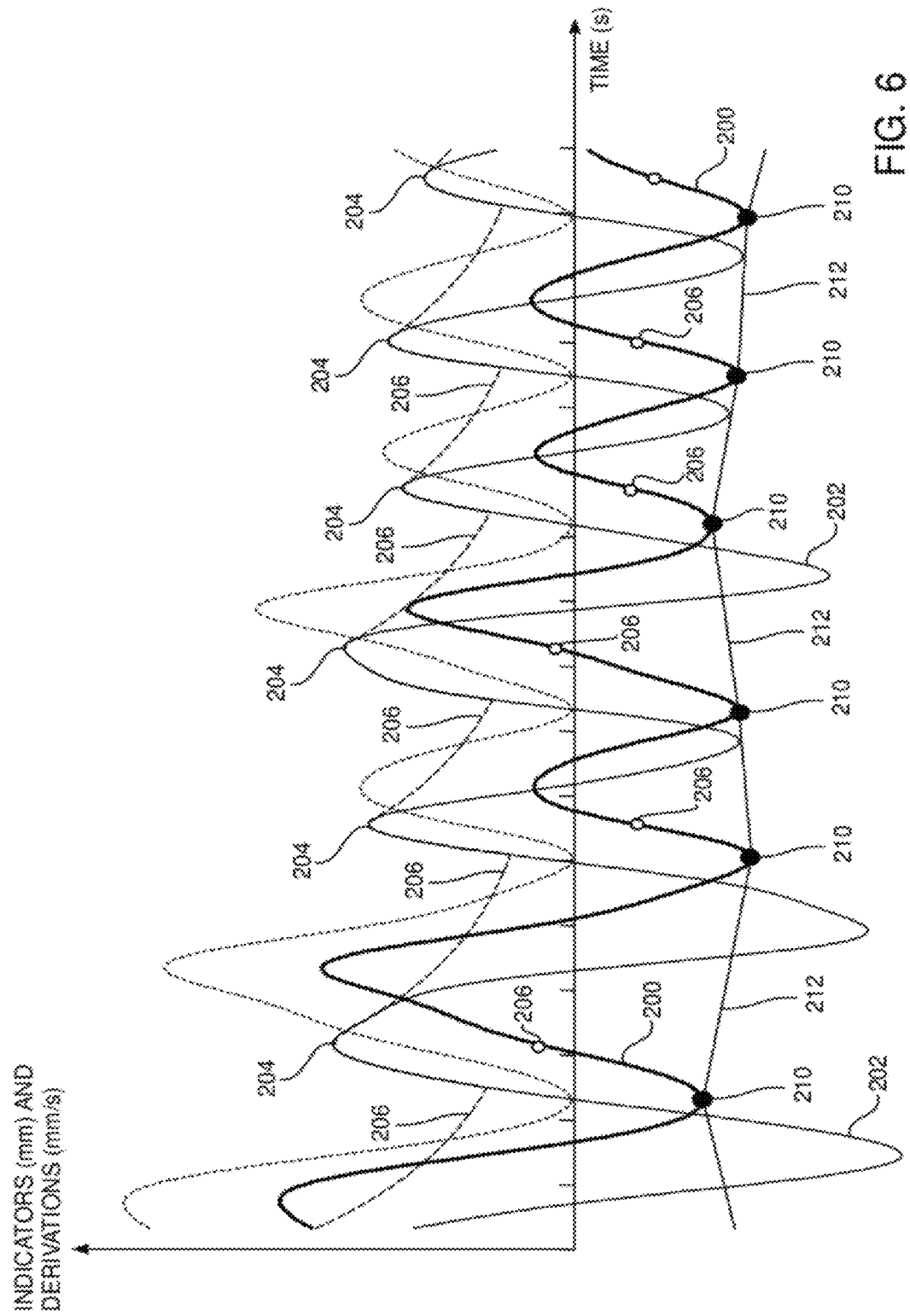

RESPIRATORY EFFECT REDUCTION IN CATHETER POSITION SENSING

FIELD OF THE INVENTION

The present invention relates generally to sensing the position of an object placed within a living body, and specifically to detection and compensation for respiration effects.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized. In these systems compensation for effects of respiration may be required.

U.S. Patent Application 2009/0030307, to Govari et al., whose disclosure is incorporated herein by reference, describes a method for position tracking that includes placing an internal reference probe in a reference location within a heart of a subject, and collecting and processing location coordinates of the probe during one or more respiratory cycles so as to define a range of the location coordinates corresponding to the reference location.

U.S. Pat. No. 6,711,429, to Gilboa et al., whose disclosure is incorporated herein by reference, describes a system and method of displaying at least one point-of-interest of a body during an intra-body medical procedure. The display may be effected by monitoring and displaying the catheter's location throughout a respiratory cycle and also averaging its location over at least one respiratory cycle.

US Patent Application 2009/0182224, to Shmarak et al., whose disclosure is incorporated herein by reference, describes apparatus for generating an organ timing signal relating to an inspected organ within the body of a patient. The disclosure refers to reconstructing a respiratory trajectory.

SUMMARY OF THE INVENTION

An embodiment of the present invention provides a method, including:

positioning body-electrodes in galvanic contact with a body of a patient;

locating a probe in the body of the patient;

tracking positions of the probe during respiration of the patient;

determining indications related to impedances between the body-electrodes during the respiration;

calculating a function relating the positions of the probe to the indications; and applying the function to identify end-expirium points of the respiration based on subsequent indications related to the impedances.

Typically, identifying the end-expirium points includes evaluating that the function is less than a predetermined threshold.

In a disclosed embodiment, tracking the positions of the probe includes determining the positions using an electromagnetic tracking system. Alternatively or additionally, tracking the positions of the probe includes computing the positions in response to currents between the probe and the body-electrodes.

In another disclosed embodiment, determining the indications includes measuring respective currents between the probe and the body-electrodes. Alternatively or additionally, determining the indications includes formulating a matrix relating the impedances between the body-electrodes to the positions of the probe.

Formulating the matrix may include determining a direction of the respiration. The method may further include determining the end-experium points for the respiration in response to the matrix and the direction. The method may yet further include determining the end-experium points for the respiration in response to a rate of change of the indications, the matrix, and the direction.

There is further provided, according to an embodiment of the present invention, apparatus, including:

body-electrodes which are positioned in galvanic contact with a body of a patient;

a probe located in the body of the patient; and a processor, which is configured to:

track positions of the probe during respiration of the patient, determine indications related to impedances between the body-electrodes during the respiration, calculate a function relating the positions of the probe to the indications, and apply the function to identify end-expirium points of the respiration based on subsequent indications related to the impedances.

The present disclosure will be more fully understood from the following detailed description of the embodiments thereof, taken together with the drawings, in which:

BRIEF DESCRIPTION OF THE DRAWINGS

FIG. 6 shows schematic graphs of a projected respiration indicator, and parameters derived from the projected indicator, vs. time, according to an embodiment of the present invention.

DETAILED DESCRIPTION OF EMBODIMENTS

Overview

An embodiment of the present invention provides a method for determining the location of a probe within the body of a patient, typically a subject undergoing a medical procedure.

The method compensates for errors in the measured location that are caused by respiration of the patient.

In order to compensate for the respiration, a probe is located in the body of the patient, and body-electrodes are positioned in galvanic contact with the patient's body. A processor tracks positions of the probe during respiration of the patient. In addition, the processor measures currents between an electrode of the probe and the body-electrodes. From the currents the processor derives indications of impedances between the body-electrodes, as respiration indicators, during the respiration. The processor generates an optimal correlation of a parameterized function of the indicators with the probe positions. The parameterized function may be expressed as a matrix correlating the positions and the respiration indicators.

Once the matrix has been determined, it may be used to determine one or more end-experium times in the respiration cycle.

System Description

The following description assumes by way of example, and at least in part, an embodiment having two position-determining coordinate sub-systems. A first, electromagnetic (EM), coordinate sub-system determines a position of a catheter probe in a subject by measuring magnetic fields at the probe. A second, current, coordinate sub-system determines the position of the probe by measuring currents from the probe to different electrodes or patches on the subject. The second sub-system is also herein termed the advanced current location (ACL) sub-system. The two coordinate sub-systems are registered with each other, as described hereinbelow, by using a hybrid catheter probe which is able to measure the magnetic fields for the EM sub-system and to act as a source for the currents of the ACL sub-system.

However, while use of the two coordinate sub-systems may be advantageous, it is not a requirement for embodiments of the present invention. Rather, embodiments of the present invention only require one coordinate system such as the ACL sub-system described herein.

Aspects of a tracking system similar to the ACL sub-system described herein are described in U.S. Patent Application 2010/0079158 to Meir Bar-Tal et al., which is assigned to the assignee of the present application and which is incorporated herein by reference.

Figure 1A:
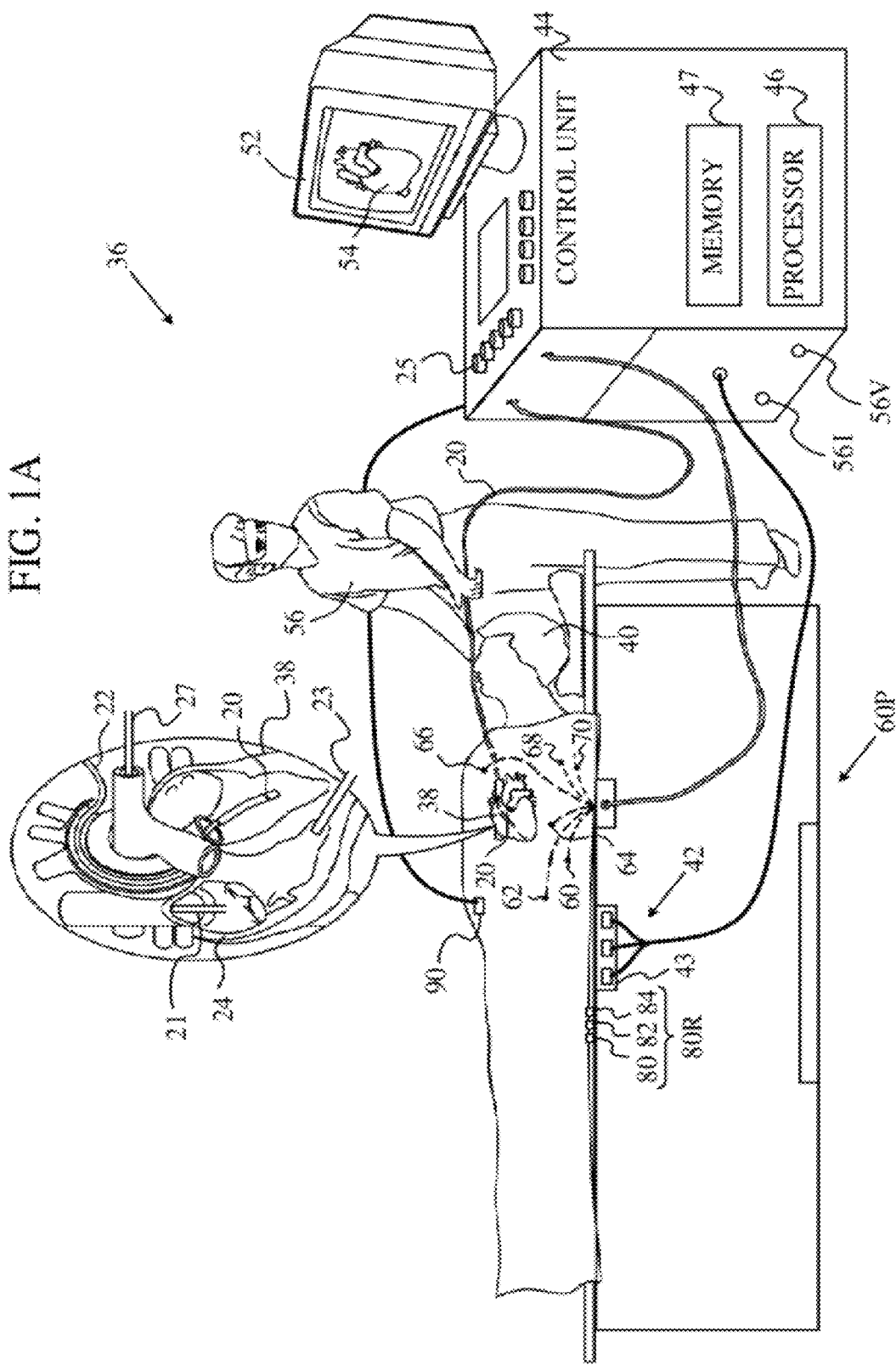
FIG. 1A is a schematic, pictorial illustration of a position sensing system, utilizing a hybrid catheter probe.
Figure 1B:
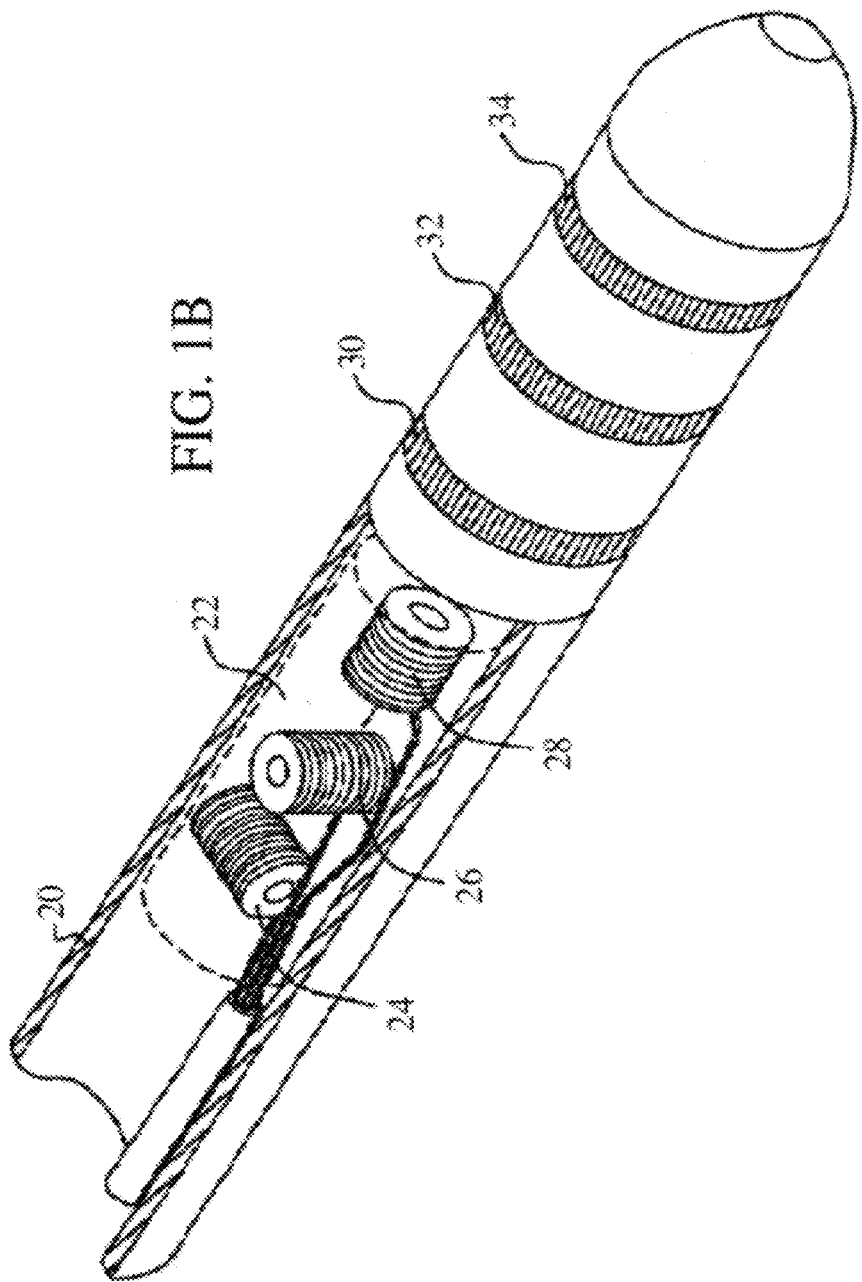
FIG. 1B is a schematic detailed view showing the distal end of the hybrid catheter, according to an embodiment of the present invention.

FIG. 1A is a schematic, pictorial illustration of a position sensing system 36, utilizing a hybrid catheter probe 20, and FIG. 1B is a schematic detailed view showing the distal end of the hybrid catheter, according to an embodiment of the present invention. The hybrid catheter may also be referred to herein as a mapping-catheter. A medical professional 56 is assumed to operate system 36.

By way of example, except where otherwise stated in the description hereinbelow, mapping-catheter 20 is assumed to be used in an invasive procedure within a chamber of a heart 38 of a patient 40, also referred to herein as subject 40. Alternatively, position sensing system 36 may be used with probes similar to catheter 20 in other body cavities. Subject 40 is placed in a magnetic field generated, for example, by positioning under the subject a location pad 43 containing magnetic field generator coils 42. The magnetic fields generated by coils 42 generate electrical signals in coils 24, 26 and 28 of an electromagnetic (EM) sensor 22 located at the distal end of catheter 20. The electrical signals are conveyed to a control unit 44, which analyzes the signals so as to determine the coordinates of the position and of the orientation of catheter 20. Alternatively, the coils in magnetic field sensor 22 may be driven to generate magnetic fields, which are detected by coils 42.

Control unit 44 includes a processor 46, typically a computer with appropriate signal processing circuits. The processor uses a memory 47, which typically comprises both volatile and non-volatile data storage devices, wherein data for operating system 36 is stored. The processor is coupled to drive a console 52, which may provide a visual display 54 of the location of catheter 20.

Control unit 44 comprises alternating current drivers 56I which processor 46 uses to supply currents to mapping-catheter-conductive-electrodes 30, 32, and 34 that are located at the distal end of mapping-catheter 20. Processor 46 sets the alternating frequency of the current supplied to each electrode of catheter 20 to be different. The catheter electrodes are connected by wires through the insertion tube of the catheter to current and voltage measurement circuitry in control unit 44.

The control unit is connected by wires to body surface electrodes, also referred to herein as body-electrodes, which may be any type of body electrodes known in the art, such as button electrodes, needle electrodes, subcutaneous probes, or patch electrodes. The body-electrodes are typically in galvanic contact with the body surface of subject 40, and receive body surface currents therefrom. Where the following description refers to patch electrodes or patches, it will be understood that embodiments of the present invention may use any of the other type of electrodes described above.

In some embodiments, one or more of the body-electrodes may be positioned in galvanic contact with, and inside, the body of subject 40. Typically, control unit 44 tracks the position of these internally located body-electrodes, for example by these body-electrodes being configured to have tracking coils similar to coils 24, 26 and 28 in catheter 20. Except where otherwise stated, the following description assumes, for simplicity, that the body-electrodes are located on the body of subject 40. Those having ordinary skill in the art will be able to adapt the description, mutatis mutandis, to cover body-electrodes positioned inside the body of subject 40.

By way of example, body surface electrodes are herein assumed to comprise adhesive skin patches 60, 62, 64, 66, 68 and 70, generically referred to herein as active current location (ACL) patches 60P, or by an ACL patch index "i," where i is an integer between 1 and 6. ACL patches 60P may be placed at any convenient locations on the body surface of subject 40 in the vicinity of the probe. ACL patches 60P typically have respective associated tracking coils, similar to coils 24, 26 and 28 in catheter 20. In alternative embodiments of the invention, the body surface electrodes may vary in number. The body surface electrodes receive differing mapping-currents from the electrodes of the mapping-catheter, and the differing currents are analyzed to determine a location or position of catheter 20. Catheter thus comprises two components for measuring its location, one component operating in an EM sub-system of system 36, the other component operating in an ACL sub-system of the system 36. Catheter 20 is also termed a hybrid catheter.

Control unit 44 also comprises voltage generators 56V, which are connected to ACL patches "i" by their connecting wires, and which processor 46 uses to measure the impedance of the ACL patches.

The currents from drivers 56I and generators 56V are differentiated by processor 46 operating the currents and voltages at different frequencies. Thus there are six unique frequencies for the generators supplying voltage to the ACL patches, and a multiplicity of other unique frequencies for the drivers supplying current to the catheters.

In addition, in system 36 there may be other non-hybrid catheters comprising one or more electrodes, similar to electrodes 30, 32, and 34, but not comprising a sensor such as sensor 22. Non-hybrid catheters are herein also referred to as investigation-catheters, and the electrodes of the investigation-catheters are also referred to as investigation-catheter-conductive electrodes. System 36 is able to track these investigation-catheters. By way of example, one such non-hybrid catheter 21 is shown in FIG. 1A.

In one embodiment there are approximately 90 frequencies for current drivers 561, so that up to 90 catheter electrodes may be tracked simultaneously in system 36.

Skin patches, herein assumed by way of example to comprise three adhesive skin patches 80, 82, and 84, are typically placed on the back of subject 40 for use as position references. Patches 80, 82, and 84 are herein referred to generically as reference patches 80R. Each reference patch 80R has an EM sensor, which is generally similar to sensor 22, and which provides the position of its respective patch to processor 46. Reference patches 80R are connected to control unit 44 by wires.

System 36 may also include a reference position sensor, such as an internally-placed catheter, inserted into a moving organ of body 40, herein assumed to be heart 38, and maintained in a substantially fixed position relative to the moving organ. Herein the reference sensor is assumed to comprise a coronary sinus reference catheter (CSRC) 27, and is also referred to herein as reference catheter 27. Catheter 27 may be either a hybrid or a non-hybrid catheter.

Typically, system 36 includes other elements, which are not shown in the figures for the sake of simplicity, and which are referred to as necessary in the following description. For example, system 36 may include an ECG monitor, coupled to receive signals from one or more body surface electrodes, so as to provide an ECG synchronization signal to control unit 44. Typically, system 36 also includes an ablation system operated by control unit 44.

The configuration of FIG. 1A is an example configuration, which is chosen purely for the sake of conceptual clarity. In alternative embodiments, any other suitable configuration can also be used. Typically, processor 46 comprises a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Figure 2A:
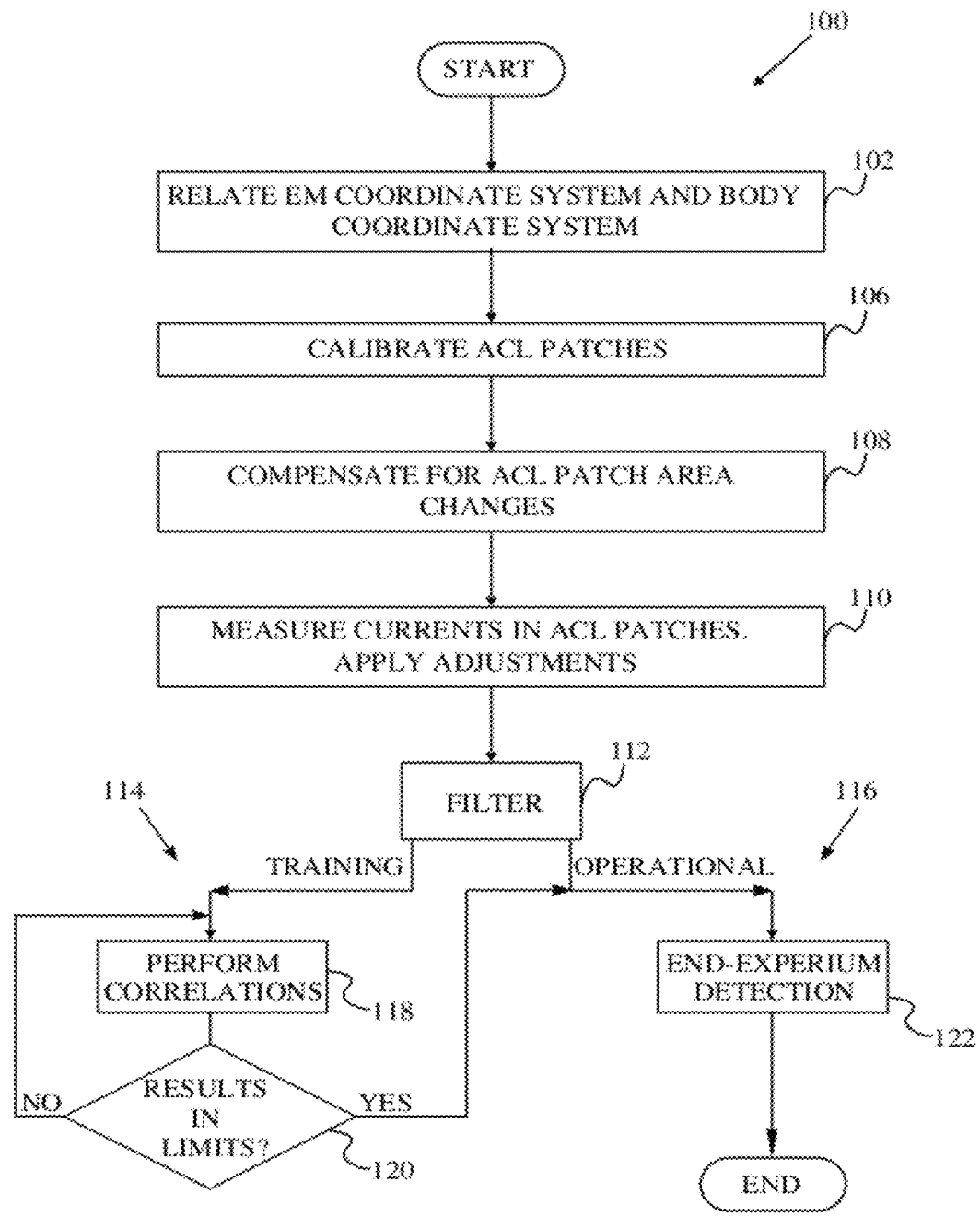
FIG. 2A is a flow chart schematically illustrating a process for operating the position sensing system.
Figure 2B:
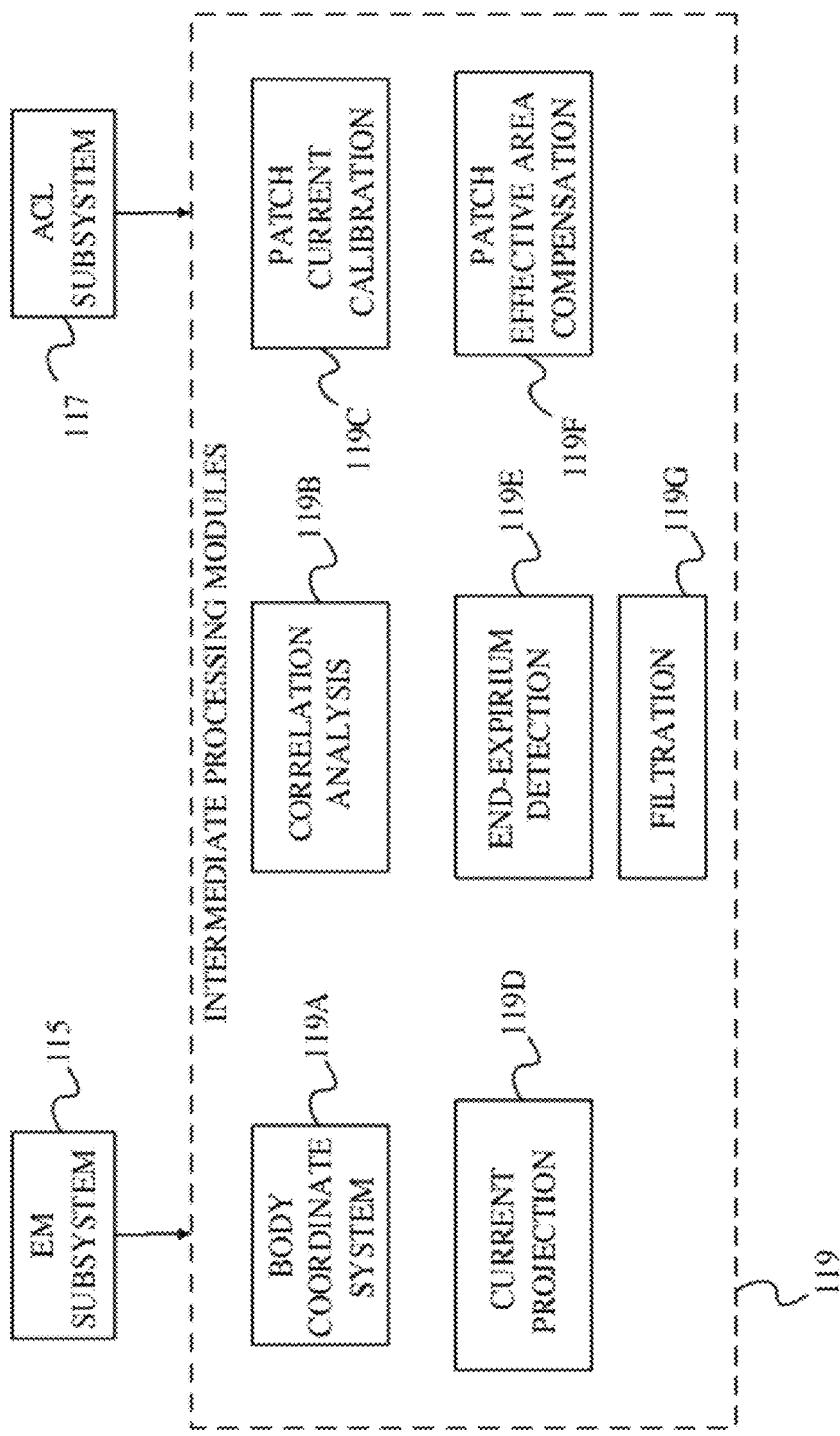
FIG. 2B is a simplified block diagram of the system, according to an embodiment of the present invention.

FIG. 2A is a flow chart 100 schematically illustrating a process for operating system 36 during performance of a procedure on a subject, and FIG. 2B is a simplified block diagram of the system, according to an embodiment of the present invention.

In a reference frame correlation step 102, coordinates measured in an EM reference frame and in an active current location (ACL) reference frame are correlated. An EM tracker sub-system 115 generates measurements in the EM reference frame; an ACL tracker sub-system 117 generates measurements in the ACL frame, also herein termed the Body Coordinate System. The EM tracker sub-system measures locations using the electromagnetic fields generated by coils 24, 26, and 28. The ACL tracker sub-system measures locations using currents through ACL patches 60P.

Except where otherwise indicated, the following steps of the flowchart are performed in intermediate processing modules 119, which comprise body coordinate system module 119A, correlation analysis module 119B, patch current calibration module 119C, current projection module 119D, end-expirium detection module 119E, patch effective area compensation module 119F, and filtration module 119G.

In an ACL patch calibration step 106, processor 46, generates currents in the ACL patches to determine differences in individual ACL patch impedances. The differences in the impedances affect the currents in the ACL patches that are measured by the processor.

Steps 102 and 106 are typically only implemented at the beginning of operation of system 36. The remaining steps of the flow chart are typically performed on a continuing basis during operation of the system.

In a patch compensation step 108 processor 46 compensates for changes in the ACL patches effective area. The changes are typically caused by factors such as change of conductivity of the patch, usually because of sweating, and partial peeling of the patch from the skin of the patient. Processor 46 uses currents similar to those generated in step 106 to determine compensation factors.

In a current projection step 110, the processor measures the currents in the ACL patches that are generated by currents injected into catheters being tracked, and applies the adjustments determined in steps 106 and 108 to the currents. The adjusted currents are used to determine preliminary positions of the catheters being tracked, as well as to determine respiration indicators. The respiration indicators are indications, based on impedance measurements, that are representative of a state of respiration of the subject undergoing the procedure.

In a filtration step 112, the time-varying positions and the time-varying respiration indicators determined in step 110 are filtered to permit only components having the very low frequencies associated with respiration to pass. Higher frequency components, such as those associated with the beating heart, are blocked. In filtration step 112, rates of change of the respiration indicators, also herein termed respiration indicator velocities, are also calculated. The filtered positions, indicators, and velocities are stored for future analysis.

After filtration step 112, the process proceeds in one of two paths. A first, training, path 114 is followed during initialization of the process. A second, operational path 116 is followed once initialization has been completed.

In training path 114, in an analysis step 118, filtered time-varying respiration indicators are correlated with filtered time-varying positions of a "training" catheter, i.e., one that is positioned in a fixed position in the heart for the duration of the training. A combination of the different indicators, which provides the best correlation with the position, is generated in the form of a correlation matrix. In addition, the respiration indicators are analyzed to determine a "most prominent direction" vector for the respiration motion.

The training, as shown by a comparison 120, typically continues until results generated by the correlation matrix are within acceptable preset limits. The comparison checks that positions generated by the correlation matrix are within preset limits of actual positions. Once the positions are within the preset limits, the flow chart transfers to operational path 116.

In a detection step 122 in the operational path, the correlation matrix and the respiration direction vector are used to analyze further incoming filtered respiration indicators (generated in step 112). The analysis estimates a gating point at which end-expirium occurs. The analysis may also include use of a threshold by processor 46 to determine if the estimation of the end-expirium point is to be classified as provisional or as final.

In a position step 124, processor 46 recalls stored training catheter positions, corresponding to the respiratory trajectory of the catheter. The trajectory is gated to the end-expirium point, and the gated trajectory is used to estimate the respiratory movement of a catheter, typically a catheter other than the training catheter. The respiratory position that is estimated in this way is subtracted from actual catheter position coordinates, to give catheter position measurements that are invariant over the respiratory cycle.

The following description explains each of the steps of flow chart 100 in detail.

Body Coordinate System

Figure 3:
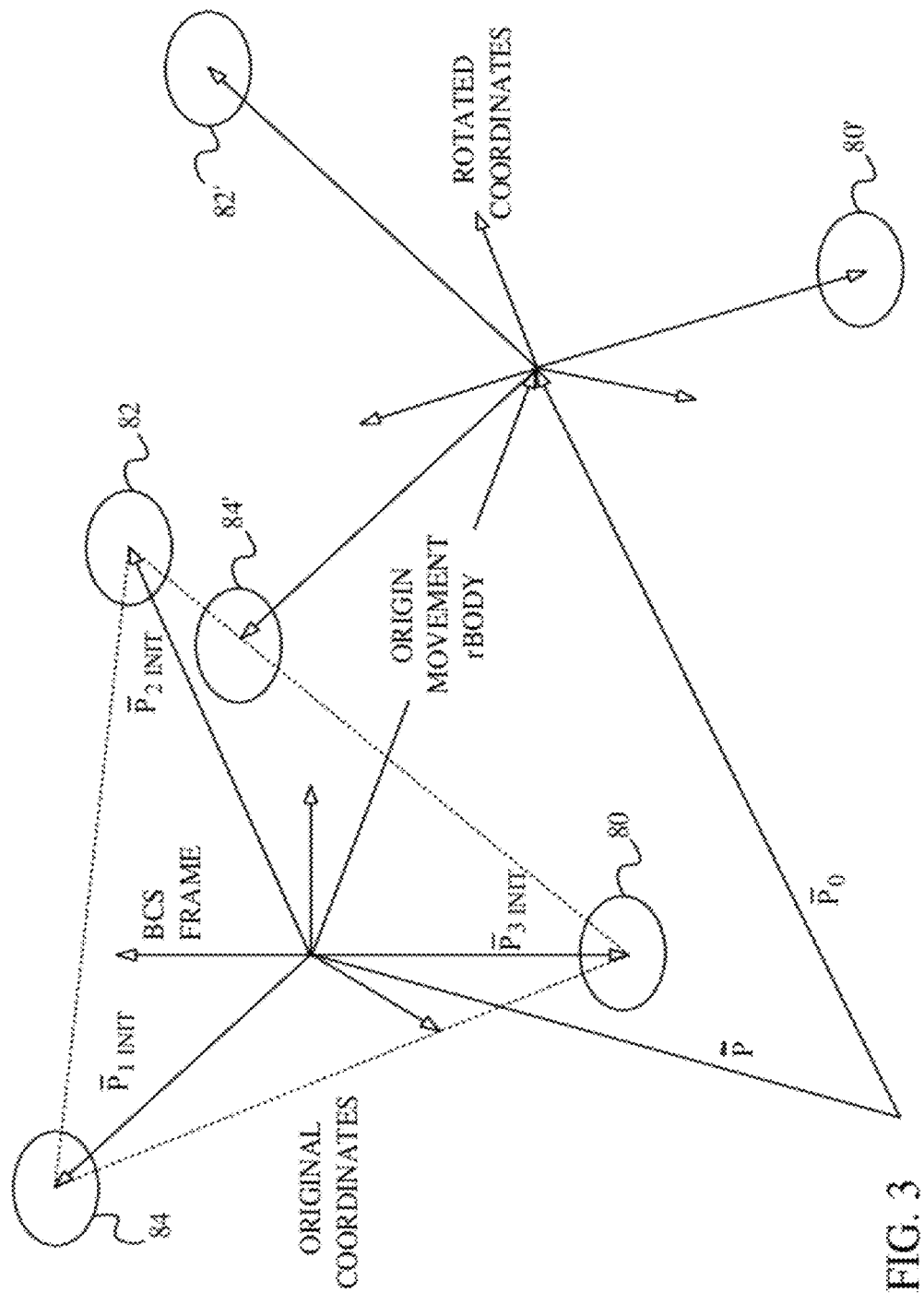
FIG. 3 is a schematic diagram illustrating a vector relationship for reference patches used in the position sensing system, according to an embodiment of the present invention.

FIG. 3 is a schematic diagram illustrating a vector relationship for reference patches 80R, according to an embodiment of the present invention. Initial positions of the patches are shown as patches 80, 82, and 84. Positions after movement are shown as patches 80', 82', and 84'.

In body coordinate system module 119A, processor 46 applies the relationship in performing reference frame correlation step 102 of flowchart 100. As stated above, system 36 comprises two tracking sub-systems: EM tracker sub-system 115 using sensors such as sensor 22, and ACL tracker sub-system 117 using currents through patches 60P. Each sub-system operates in a respective frame of reference. The EM tracker sub-system operates in an EM frame of reference that is generally fixed with respect to pad 43. The ACL tracker sub-system operates in an ACL frame of reference, the body coordinate system (BCS), that is assumed to be generally fixed with respect to patches 80R. Patches 80R enable measurements made in one of the sub-systems to be converted to the other sub-system. Reference patches 80R are attached to the back of subject 40, so that any motion of the subject with respect to pad 43 is reflected in signal changes in the EM sensors of the reference patches.

Initially, processor 46 analyzes signals from the EM sensors on reference patches 80R, to determine an initial frame of reference for the BCS. Typically, after the initial frame has been determined, the processor analyzes signals from the EM sensors periodically, to determine changes in the location and orientation of the BCS frame of reference. The processor is able to detect if system parameters have changed beyond those expected, and in this event may return to process followed initially.

Initially, the processor accumulates the location of patches 80R in LP coordinates, i.e., coordinates measured relative to location pad (LP) 43, for a time patchInitTime, typically approximately 1 sec.

The processor then calculates the mean location and the standard deviation for each patch:

$$\tilde{\vec{P}1} = \frac{1}{N}\sum_i^N \vec{P1}_i \quad (1)$$

$$\vec{P1}_{STD} = \sqrt{\sum_i^N \frac{1}{N}\left(\vec{P1}_i - \tilde{\vec{P1}}\right)^2},$$

where i is a sample index,
N is the number of samples in time patchInitTime
$\vec{P1}_i$ is a sample value,
$\tilde{\vec{P1}}$ is the mean value of $\vec{P1}_i$ for each patch l, and
$\tilde{\vec{P1}}_{STD}$ is the standard deviation of $\tilde{\vec{P1}}$.

Providing the value of each $\tilde{\vec{P1}}_{STD}$ is less than a preset figure, typically approximately 1 mm, the calibration is accepted, in which case the mean $\tilde{\vec{P}}$ of all the means is set as the origin the BCS:

$$\tilde{\vec{P}} = \frac{1}{3}\sum_1^3 \tilde{\vec{P1}} \quad (2)$$

The radius vector from each patch to the origin is also calculated and saved for further use:

$$\vec{P}l_{init} = \tilde{\vec{P1}} - \tilde{\vec{P}} \quad (3)$$

The mean vector defined by equation (2) and the three vectors defined by equation (3) are illustrated in FIG. 3. In addition to the origin, as defined by equation (2), the three vectors of equation (3) define a triangle in a plane, shown in the figure by broken lines between patches 80, 82, and 84. The initial BCS x, y, and z axes are defined using the triangle.

During operation of system 36, patches 80R may move, as exemplified by patches 80', 82', and 84', and processor 46 measures the new positions of the patches periodically, typically with a period of the order of one second. Embodiments of the present invention assume that the axes defined in the calibration phase move as an approximately rigid body, and processor 46 determines the translation and rotation of the axes from the new patch 80R positions during the tracking phase. Prior to the determinations, the new patch positions are filtered to reduce noise, the filtering typically comprising a low pass filter of the type:

$$y_i = ay_{i-1} + (1-a)x_i, \quad (4)$$

where $y_i$, $y_{i-1}$ are current and previous position estimates,
$x_i$ is the current position measurement, and
a is a factor between 0 and 1.

Typically "a" in equation (4) is selected so that there is an effective time constant of approximately 0.5 s in determining current position estimates $\vec{P1}$. Consequently, since body motion is usually slow, such a time constant does not significantly affect performance of system 36.

The filtered positions $\vec{P1}$ are used to determine a new origin vector of coordinates $\vec{P}_O$, substantially as described above for equation (3).

From the filtered positions $\vec{P1}$ processor 46 also determines a rotation matrix T, by methods which will be apparent to those having ordinary skill in the art, relating a new orientation of the axes with the original axes orientation. The processor then applies equation (5) (below) to transform each catheter tip location measurement back to the original BCS axes.

$$\vec{p}b = T^T \cdot (\vec{p} - \vec{P}_O) \quad (5)$$

where $T^T$ is the transpose of T,
$\vec{p}$ is a vector representing a measured catheter tip location, and
$\vec{p}b$ is a vector of the catheter tip relative to the original BCS axes.

The vector p is calculated in position step 124.

Patch Current Calibration

Ideally the impedance of each ACL patch measured to ground is zero, but this may not be the case in practice. If the impedances are different from zero, the measured currents through the patches may lead to errors in the predicted location of a catheter such as catheter 20, so that to reduce such errors, processor 46 uses a patch current calibration module 119C to perform a calibration on the ACL patches in patch calibration step 106 (FIGS. 2A and 2B). The calibration compensates for the impedances being non-zero, and also for differences in the impedances between the patches. The calibration enables processor 46 to estimate the current that would flow in a patch if the patch impedance is zero.

Figure 4:
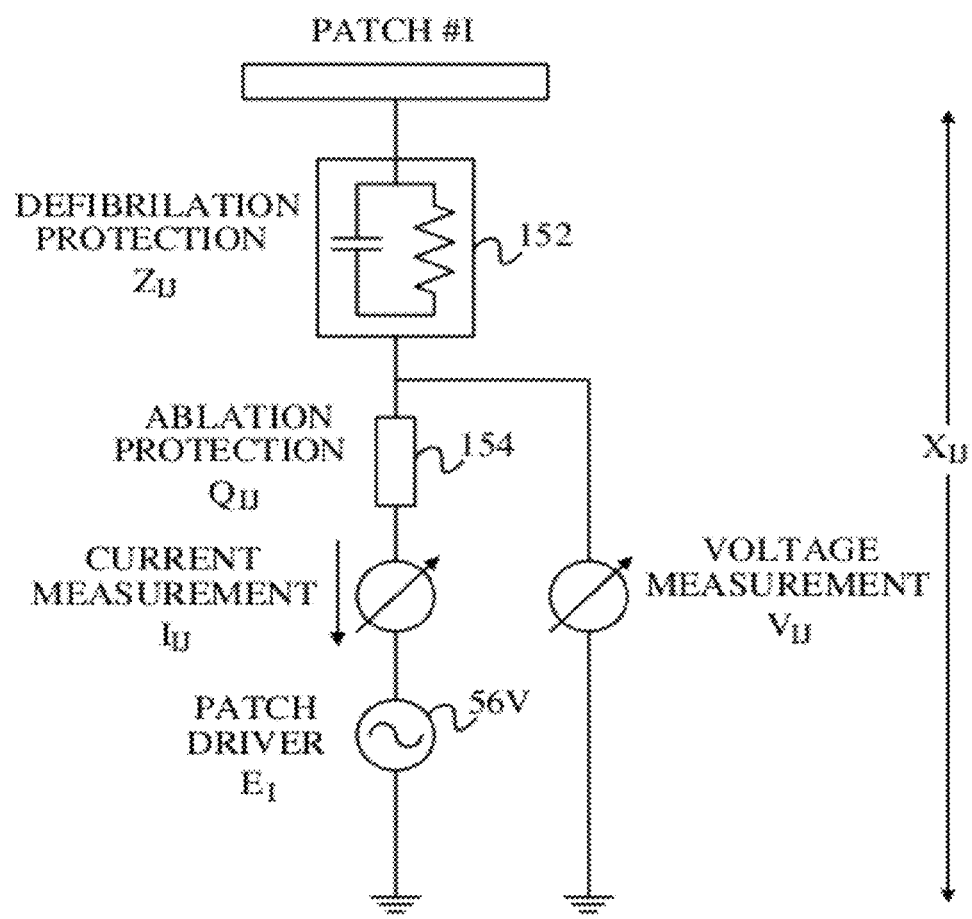
FIG. 4 is a schematic illustration of an active current location (ACL) patch circuit, according to an embodiment of the present invention.

Reference is now made to FIG. 4, which is a schematic illustration of an ACL patch circuit, according to an embodiment of the present invention.

All ACL patches have generally similar circuits. Each ACL patch i comprises a defibrillation protection circuit 152 and an ablation protection circuit 154. The two circuits are connected in series between the patch and ground. In FIG. 4, and for the analysis below, for each patch i, j is a frequency index, denoting the frequency $f_j$ transmitted by the patch.

$z_{ij}$ is a known impedance of defibrillation protection circuit 152. The known impedance may typically be provided by a patch box manufacturer, or determined from analysis of circuit 152.

$q_{ij}$ is the impedance of ablation protection circuit 154. The ablation protection circuit impedance is estimated during a patch impedance calibration process, described below.

$E_i$ is a voltage, from a voltage source 56V, that drives patch i with frequency $f_i$.

$I_{ij}$ is a current measured through patch i at frequency $f_j$.
$V_{ij}$ is a voltage measured on patch i at frequency $f_j$.
$X_{ij}$ is the actual voltage on patch i at frequency $f_j$.

In a patch impedance calibration procedure for system 36, processor 46 uses a respective voltage source 56V to inject current into each patch i at a corresponding frequencies $f_i$. The injected currents are also used in a patch effective area compensation procedure, described below.

The processor applies the two procedures referenced above, i.e., the patch impedance calibration procedure, and the patch effective area compensation procedure, typically while the training path, described above, is being followed. The processor may also apply, as necessary, the two procedures while the operational path is being followed.

The currents are injected at different frequencies j, and console 52 comprises ADCs (analog-to-digital circuits) which processor 46 multiplexes to measure values of $V_{ij}$ sequentially and values of $I_{ij}$ simultaneously.

In the patch impedance calibration procedure the processor estimates a value of $q_{ij}$ from the values of $V_{ij}$ and $I_{ij}$, typically by finding the ratio $$\frac{V_i}{I_i}$$

at each frequency j, and finding a best fit, typically a best quadratic fit, across the measured frequencies. Thus:

$$q_{ij} = \hat{q}_i(f_j) = \left[\frac{\hat{V}_{ij}}{I_{ij}}\right] \tag{8}$$

During the tracking phase, processor 46 measures the values of $I_{ij}$ and $$\sum_i V_{ij}$$

at the different operating frequencies f. In the following analysis, the expressions of equation (9) are assumed.

$$\tilde{V}_j \equiv \sum_i V_{ij}, \text{ and} \tag{9}$$

$$E_{ij} \equiv \delta_{ij} E_j$$

where $\tilde{V}_j$ is the sum of voltages measured on all patches at a frequency $f_j$, and $\delta_{ij}$ is the Kronecker delta.

For a particular patch i being driven at a frequency j, applying Ohm's law to ablation protection circuit 154 gives:
$V_{ij} = E_{ij} + q_{ij} I_{ij}$, so that $$\tilde{V}_j \equiv \sum_i V_{ij} = \sum_i (E_{ij} + q_{ij} I_{ij}) = \sum_i (\delta_{ij} E_j + q_{ij} I_{ij}) = E_j + \sum_i q_{ij} I_{ij}$$

which rearranged gives:

$$E_j = \tilde{V}_j - \sum_i q_{ij} I_{ij} \tag{10}$$

Applying Ohm's law and equation (10) to the complete circuit of FIG. 4 gives, for a particular patch i:

$$X_{ij} = E_{ij} + (q_{ij} + z_{ij}) I_{ij} = \tag{11}$$

$$\delta_{ij} E_j + (q_{ij} + z_{ij}) I_{ij} = \delta_{ij}\left(\tilde{V}_j - \sum_k q_{kj} I_{kj}\right) + (q_{ij} + z_{ij}) I_{ij}$$

where $X_{ij}$ is the overall voltage on patch i at frequency j.

The values of equation (11) may be used to determine a body conductance matrix σ, where σ is defined by the matrix equations:

$$-I = \sigma \cdot X, \text{ or } \sigma = -I \cdot X^{-1} \tag{12}$$

where I is a matrix of patch currents, and X is a matrix of patch voltages.

The patch currents may also be written as a vector s. The negative sign in equation (12) assumes a convention that positive current flows into body 40, and positive currents are also measured flowing out of the body. Alternatively, an equation similar to equation (12), using an impedance matrix Im, may be written relating matrices I and X.

Those having ordinary skill in the art will understand that a system conductance matrix σ', which is a combination of the body conductance matrix σ and a patch resistance matrix $R_k$, is given by:

$$\sigma' = (Id + \sigma \cdot R_k)^{-1} \cdot \sigma \tag{13a}$$

where Id is the identity matrix
σ is the conductance matrix defined in equation (12), and
$R_k$ is a diagonal matrix of patch resistances, with $(z_{ik} + q_{ik})$ as the $i^{th}$ diagonal element, for a catheter transmitting a frequency $f_k$.

If a voltage V is applied to the system, the current flowing in the system is given by:

$$\tilde{s} = \sigma' \cdot V = (Id + \sigma \cdot R_k)^{-1} \cdot \sigma \cdot V \quad (13b)$$

where V is a voltage vector, and
$\tilde{s}$ is the measured current vector at frequency $f_k$.

Equation (13b) shows that is affected by the patch resistances. A calibrated current, that does not depend on the patch resistances and thus does not depend on frequency $f_k$, may be defined as:

$$s = \sigma \cdot V = (Id + \sigma \cdot R_k) \cdot \tilde{s} \quad (13c)$$

where s is a calibrated current vector.

Processor 46 passes the estimated current values in each patch given by vector s to a patch effective area compensation process, described below.

Patch Effective Area Compensation

The description in this section explains patch compensation step 108 (FIG. 2A). In step 108 processor 46 uses patch effective area module 119F to perform a process that compensates for changes in the effective area of ACL patches i. In this section, patches 60P are differentiated by being referred to as patch i and patch j. Some causes of changes to the effective area of the ACL patches are partial peeling of a patch from patient body 40, and skin conductivity changes, typically due to sweating. A patch effective area compensation model assumes that $$R_{ij} = G \cdot C_i \cdot C_j \cdot d_{ij} \quad (14)$$

where $R_{ij}$ is the impedance between patch i and patch j.
$C_i$, $C_j$ are effective areas of patch i and patch j
$d_{ij}$ is the distance between patches i and j, and
G is a constant of proportionality which is a function of, inter alia, medium conductivity.

In implementing the area compensation process, processor 46 generates a current $I_j$ from source patch j, and measures each of the currents $I_{ij}$ received in the other patches. Processor 46 performs the process for each ACL patch, so that for N patches, the processor makes a total of N(N−1) current measurements.

An estimated impedance $m_{ij}$ between any two patches j, is given by:

$$m_{ij} = \frac{V_j}{I_{ij}} \quad (15)$$

where $V_j$ is the voltage driving patch j.

From equation (15) a normalized estimated impedance $\hat{m}_{ij}$ is given by:

$$\hat{m}_{ij} = \frac{m_{ij}}{\sum_{\substack{k=1,\\k\neq j}}^{k=N} m_{kj}} = \frac{V_j/I_{ij}}{\sum_{\substack{k=1,\\k\neq j}}^{k=N} V_j/I_{kj}} = \frac{1/I_{ij}}{\sum_{\substack{k=1,\\k\neq j}}^{k=N} 1/I_{kj}} \quad (16)$$

Processor 46 calculates and stores the values of mid using equation (16) during implementation of the area compensation process.

The current $I_j$ generated at patch j divides between the other patches in inverse proportion to the impedance between patch j and the other patches. Thus, the current $I_{ij}$ from source patch j to receiving patch i is given by:

$$I_{ij} = I_j \frac{1/R_{ij}}{\sum_{k,k\neq j} 1/R_{kj}} \quad (17)$$

Substituting equation (14) into equation (17) gives:

$$I_{ij} = \frac{I_j}{GC_iC_jd_{ij}\sum_{k,k\neq j} 1/(GC_kC_jd_{kj})} = \frac{I_j}{C_id_{ij}\sum_{k,k\neq j} 1/(C_kd_{kj})} \quad (18)$$

Substituting the value for $I_{ij}$ into equation (16), and simplifying, gives:

$$\hat{m}_{ij} = \frac{C_id_{ij}}{\sum_{n,n\neq j} C_nd_{nj}} \quad (19)$$

where n is an integer from 1 to N, and N is the number of ACL patches.

Equation (19) may be written:

$$\sum_{n,n\neq j}(\hat{m}_{ij} - \delta_{ij})C_nd_{nj} = 0 \quad (20)$$

As described above, processor 46 has determined the values of the relative impedances $\hat{m}_{ij}$.

In equation (20), inter-patch distances $d_{ij}$ may be measured using their respective associated tracking coils (and, when i=j, $d_{ij}$=0).

Equation (20) is a system of N(N−1) equations with N unknowns, i.e., the values $C_1, C_2, \ldots, C_N$. The system of equations (20) may be used to find the relative values of $C_i$.

The system of equations is of the type $A \cdot \vec{C} = 0$ wherein A is an N(N−1)×N matrix that depends on $\hat{m}_{ij}$ and $d_{ij}$, and wherein $\vec{C}$ is a vector representing the N values of $C_i$. Singular value decomposition (SVD) analysis of A or eigenvector analysis of the N×N matrix $A^TA$ provides a solution for $\vec{C}$, as is known in the art.

Assuming that processor 46 performs eigenvector analysis of the matrix $A^TA$, the processor selects the eigenvector with the smallest eigenvalue. Typically, the values of $\hat{m}_{ij}$ and $d_{ij}$ for matrices A and $A^T$ are filtered with a filter similar to equation (4), where the filter is adjusted to have a time constant of the order of 10 seconds. The smallest eigenvector corresponds to normalized values of the 6 areas $C_i$, herein termed $Ea_i$. Typically, processor 46 calculates the values of $Ea_i$ periodically, with a period that may be set by operator 56. In one embodiment, the period is of the order of 1 second.

The estimated current vector s, derived from equation (13c), gives 6 respective values of the currents $I_i$ in the ACL patches. To compensate for the patches effective area, $Ea_i$, processor 46 forms a normalized value of each of the currents:

$$In_i = \frac{I_i \cdot Ea_i}{\sum_{i=1}^{i=6} I_i \cdot Ea_i} \equiv (In6) \quad (21)$$

where (In6) is a six-dimensional current vector.

The normalization removes effects caused by changes in effective resistance in the region of the catheter electrode, such as may be caused by the electrode coming into contact with tissue, inhomogeneity of material surrounding the electrode, and/or instability of the source injecting current into the catheter electrode.

Current Projection

The 6 currents given by equation (21) have only five degrees of freedom since their sum is always one. To prevent singularities in further analysis of the currents, in current projection step 110 the 6 currents are converted, using a projection matrix J, to five independent quantities in current projection module 119D. Projection matrix J is derived by orthogonalization of a matrix, $$\begin{pmatrix} 1 & 1 & 1 & 1 & 1 & 1 \\ 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{pmatrix},$$

taking only the last five row vectors of the resulting matrix.

After orthogonalization, the last five rows of the orthogonalized matrix give:

$$J = \begin{pmatrix} -\frac{1}{\sqrt{30}} & \sqrt{\frac{5}{6}} & -\frac{1}{\sqrt{30}} & -\frac{1}{\sqrt{30}} & -\frac{1}{\sqrt{30}} & -\frac{1}{\sqrt{30}} \\ -\frac{1}{2\sqrt{5}} & 0 & \frac{2}{\sqrt{5}} & -\frac{1}{2\sqrt{5}} & -\frac{1}{2\sqrt{5}} & -\frac{1}{2\sqrt{5}} \\ -\frac{1}{2\sqrt{3}} & 0 & 0 & \frac{\sqrt{3}}{2} & -\frac{1}{2\sqrt{3}} & -\frac{1}{2\sqrt{3}} \\ -\frac{1}{\sqrt{6}} & 0 & 0 & 0 & \sqrt{\frac{2}{3}} & -\frac{1}{\sqrt{6}} \\ -\frac{1}{\sqrt{2}} & 0 & 0 & 0 & 0 & \frac{1}{\sqrt{2}} \end{pmatrix} \quad (22)$$

The currents from equation (21) are thus projected to five current-equivalents according to equation (23):

$$(In5)=J \cdot (In6) \quad (23)$$

In addition to performing the normalization of equation (23), in current projection step 110 processor also normalizes respiration indicators. The respiration indicators are measures of changes in resistance between ACL patches caused by the respiration of the patient. The respiration indicators are generally similar in properties to the patch effective areas ($C_i$), and an expression for the indicators is derived using equation (20). From equation (20), $$C_i = \frac{\hat{m}_{ij}}{d_{ij}} \sum_n C_n d_{nj} (i \neq j) \quad (24)$$

Averaging equation (24) over j, and assuming as an approximation that $d_{ij}=1 (i \neq j); d_{ij}=0 (i=j)$, we define a respiration indicator $RI_i$ for patch i as:

$$RI_i = \sum_j \hat{m}_{ij} \sum_n R_n \hat{d}_{nj} = \sum_n R_n \left( \sum_n \hat{m}_{ij} \hat{d}_{nj} \right) \quad (25)$$

Assuming $RI_i$ is written as an N-dimensional vector $\vec{RI_i}$, $\hat{m}_{ij}$ may be written as an N×N matrix M, with 0 at the diagonals, and $\hat{d}_{ij}$ may be written as a matrix D, given by equation (26):

$$D = \begin{pmatrix} 0 & 1 & 1 & 1 & 1 & 1 \\ 1 & 0 & 1 & 1 & 1 & 1 \\ 1 & 1 & 0 & 1 & 1 & 1 \\ 1 & 1 & 1 & 0 & 1 & 1 \\ 1 & 1 & 1 & 1 & 0 & 1 \\ 1 & 1 & 1 & 1 & 1 & 0 \end{pmatrix} \quad (26)$$

In this case processor 46 iteratively estimates a new vector $RI_{i,t}$ from a previous estimate $RI_{i,t-1}$ and a new measurement $\hat{m}_{ij}$ according to the two step process:

$$\overline{RI_{i,t}} = M^T \cdot D \cdot RI_{i,t-1}, \text{ then} \quad (27)$$

$$RI_{i,t} := \frac{\overline{RI_{i,t}}}{\sum_i RI_{i,t}}$$

where t is a parameter indicating the sequential order of $RI_{i,t}$ and $RI_{i,t-1}$.

Vector $RI_{i,t}$ is six-dimensional, but has only five degrees of freedom (as in the currents of equation (21)). As shown in equation (28) below, the values of $RI_i$ derived from equation (27) are further converted in the same manner as the currents of equation (21), by multiplying by matrix J, to give a five-dimensional respiration indicator vector.

$$(RI_i 5)=J \cdot (RI_i 6) \quad (28)$$

Filtration

Figure 5:
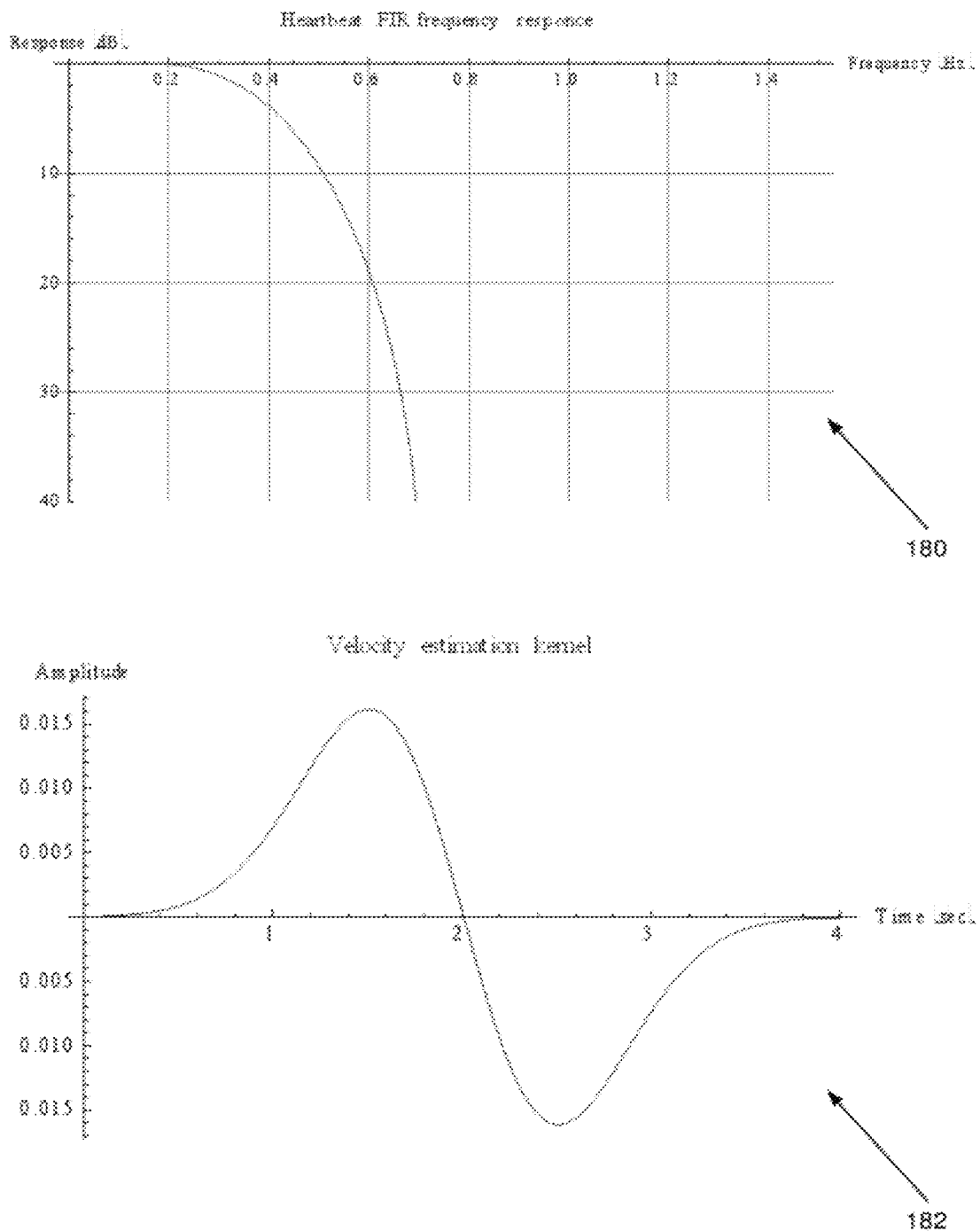
FIG. 5 shows exemplary graphs of filters used by a filtration module of the position sensing system, according to an embodiment of the present invention.

FIG. 5 shows exemplary graphs of filters used by filtration module 119G, according to an embodiment of the present invention. Filtration step 112, implemented in module 119G, filters both the locations derived from the EM system, i.e., the values of $\vec{p}b$ as given by equation (5), and the five-dimensional respiration indicator vector ($RI_i 5$) given by equation (28). Hereinbelow, for simplicity, the respiration indicator vector ($RI_i 5$) is also referred to as (RI), having five elements RI. The filtration typically uses a very low pass filter, with a sharp transition between passing and rejected frequencies, so as to preserve only the respiratory frequencies of the signals, while removing frequencies due to the heart beat. In one embodiment, module 119G comprises a finite element response (FIR) filter which has a 0 dB rejection for frequencies less than 0.2 Hz and a 40 dB or greater rejection for frequencies greater than 0.7 Hz, as shown in a graph 180.

In module 119G values of the respiration indicators produced by the FIR filter are also adjusted so that they are centered around zero (so that there is no "DC" component attached to the RI values). The adjustment may be made using a low pass filter such as is defined by equation (29) to estimate an adjustment value.

$$y_i = a y_{i-1} + (1-\alpha) x_i, \quad (29)$$

where $y_i$, $y_{i-1}$ are current and previous adjustment values,
$x_i$ is the current RI measurement, and
α is a factor between 0 and 1. α is typically selected so that there is an effective time constant of approximately 1 s in determining current adjustment values.

The values of $y_i$ from equation (29) are subtracted from the values of RI produced by the FIR filter, to remove the RI DC component. The filtered, adjusted respiration indicator vector is herein termed (RIa).

Module 119G also calculates respiration velocities, i.e., rates of change of the respiration indicators, and filters the velocities. In one embodiment, the differentiation and filtration of the respiration indicators RI is produced by convolving the indicators with a velocity kernel. The velocity kernel may be derived from differentiation of a Gaussian function, and a graph of a typical velocity kernel v is given in a graph 182. The convolution is according to equation (30):

$$Rv = RI(x) \, v \qquad (30)$$

where Rv is the velocity of respiration indicator RI.

Analysis

During the initialization mode, i.e., in training path 114, values from filtration module 119G are analyzed in analysis step 118. The analysis uses correlation analysis module 119B. At the start of initialization, typically at the beginning of a medical procedure, professional 56 positions a reference sensor, herein assumed to be CSRC 27, in a relatively fixed position in heart 38. The sensor is typically left in this position for two or more respiration cycles, i.e. for a time period of approximately 30 s, herein termed the training period.

During the training period, processor 46 saves position values generated by CSRC 27, and the filtered, adjusted respiration indicators RIa. Since the correlations performed by module 119B are with regard to motion due to respiration, measurements are performed with respect to a mean of the reference sensor's position, determined according to equation (31):

$$\vec{r}_i = \vec{p}_i - \frac{1}{K}\sum_1^K \vec{p}_i \qquad (31)$$

where:
$\vec{p}_i$ is the sensor position for sample i, and
$\vec{r}_i$ is the adjusted sensor position for sample i, and
K is the total number of samples in the training period.

To avoid using position and respiration indicator values that may be very distant from a central value, e.g., they may have been obtained during sudden motion of the sensor, the filtered positions are sorted to remove such values. In one embodiment the absolute values of $\vec{r}_i$ are assumed to lie between 0 and 20 mm, and the absolute values are sorted into a histogram with 1 mm width bins. Only positions, and associated respiration indicators, within a user-selected percentile of the histogram are used in further analysis by module 119B. Typically the $90^{th}$ percentile is selected. The respiration indicator vector produced by the sorting is herein referred to as (RIas).

To prevent numerical instability in the further analysis, the elements of (RIas) are scaled to have values close to unity. The scaling may be accomplished by multiplying each of the elements of (RIas), $RIas_k$, by a common factor g, given by equation (32):

$$g = \frac{1}{\text{Max}(\text{Abs}(\overrightarrow{RIas_k}))} \qquad (32)$$

In addition to multiplying the elements of (RIas) by the factor g, a unity element is added to vector (RIas), producing a six-dimensional respiration indicator vector $(RI_k)$ having elements given by equation (33):

$$\widehat{RI}_k = \{g\overrightarrow{RIas_k}, 1\} \qquad (33)$$

A correlation between the respiration indicators $RI_k$ and the corresponding position vector $r_k$, in the form of a (3 row, 6 column) correlation matrix C, is generated from vector $(RI_k)$ and vector $r_k$ according to equation (34):

$$C = (\vec{r}_k) \cdot (\hat{RI}_k)^{-1} \qquad (34)$$

where $(\vec{r}_k)$ are stacked values of vectors $r_k$,
$(\hat{RI}_k)$ are stacked values of vectors $(RI_k)$, and
$(\hat{RI}_k)^{-1}$ is the pseudo inverse of $(\hat{RI}_k)$.

Correlation matrix C effectively parameterizes the different respiration indicators $RI_k$ so that the parameterized indicators form an optimal correlation with the position vector $r_k$.

In a final part of analysis step 118, as shown by comparison 120, matrix C is validated by estimating values of $r_k$, $\hat{r}_k$, using matrix C and corresponding values of $RI_k$, according to equation (35):

$$\hat{r}_k = C \, \widehat{RI}_k \qquad (35)$$

The estimated values, $\hat{r}_k$, are compared with the measured values of $r_k$ stored in memory 47. Providing the comparison gives a difference that is within a preset threshold limit, analysis step 118, and thus training mode 114, is assumed to be complete and correlation matrix C is used in operational mode 116. Typically, a root mean square (RMS) of the difference between the estimated and measured values of the location is less than 1 mm, and a maximum value of the difference is less than 3 mm.

If the difference between the estimated and measured values of $r_k$ is not within the preset threshold limit, the training continues.

In addition to determining correlation matrix C, analysis module 119B determines a "most prominent direction" for the respiration motion, as a respiration direction vector $\vec{rd}$. In one embodiment vector $\vec{rd}$ is calculated by stacking the adjusted sensor positions found by equation (31) into a matrix R, as in equation (36):

$$R = \begin{bmatrix} x_1 & y_1 & z_1 \\ x_2 & y_2 & z_2 \\ \vdots & \vdots & \vdots \\ x_n & y_n & z_n \end{bmatrix} \qquad (36)$$

Singular value decomposition (SVD) is applied to matrix R, and respiration direction vector $\vec{rd}$ is assumed to be equal to the eigenvector of the largest eigenvalue.

End Expirium Detection

Once the correlation matrix C and respiration direction vector $\vec{rd}$ have been determined in analysis step 118, processor 46 transfers the matrix and the respiration direction to end-expirium detection module 119E. After the transfer, processor 46 follows operational path 116 of flow chart 100. In detection step 122, implemented in module 119E, processor 46 determines when end-expirium occurs.

FIG. 6 shows schematic graphs of a projected respiration indicator, and parameters derived from the projected indicator, vs. time, according to an embodiment of the present invention. The graphs illustrate results generated in module 119E.

In step 122, processor 46 calculates, for each set of filtered indicator values derived from filtration module 119G, an indicator projected onto the most prominent respiration direction. The projection is performed according to equation (37):

$$RIp_k = \vec{rd} \cdot C \cdot \widehat{RI}_k \quad (37)$$

where $RIp_k$ is the projected indicator at a time k, and $\vec{rd}$, $C$, and $\widehat{RI}_k$ are as described above with reference to equations (36), (34), and (33).

A graph 200 shows exemplary values of RIp vs. time.

The processor also calculates a projected indicator velocity according to equation (38):

$$RIv_k = \vec{rd} \cdot C(3,5) \cdot Rv_k \quad (38)$$

where $RIv_k$ is the projected indicator velocity at a time k, $\vec{rd}$ is as described above, C(3,5) is a (3 row by 5 column) matrix derived from matrix C by omitting the last column, and $Rv_k$ is the respiration indicator velocity given by equation (30).

A graph 202 shows exemplary values of RIv vs. time.

Typically, maximum values of RIv, RIvMax, are used to determine boundaries of each respiration cycle.

Typical values of RIvMax are illustrated as points 204 on graph 202. Corresponding points on graph 200 are points 206.

In order to reduce false determinations of RIvMax, processor 46 typically ignores any maximum that is within is of a previous RIvMax value, since such a maximum may be caused by penetration of a heartbeat signal through filtration module 119G.

To further reduce false determinations of RIvMax, processor 46 may calculate a decay value with time for a given RIvMax, and may check that a subsequent RIvMax is greater than that given by the decayed value. The decaying values of RIvMax may be calculated iteratively using an equation of the form:

$$RIvMax_i = \alpha(RIvMax_{i-1} - \beta) + \beta \quad (39)$$

In one embodiment $\alpha=0.99$ and $\beta=0.5$. Typically, processor 46 prevents the decaying value from reaching zero, limiting the value to a preset lower limit.

Broken lines 208 illustrate the decaying values of RIvMax applied to each RIvMax. As is illustrated in the graphs, each subsequent point 204 is above the decaying value from the previous point 204.

Once the processor has detected a valid maximum velocity RIvMax the processor analyzes values of RIp (graph 200) (up to those corresponding to the previous RIvMax) to determine a minimum of value of RIp. These minima, shown as points 210, correspond to the end-expirium points.

The end-experium points are points in time, and the values of RIp may be corrected so that all RIp values are greater than or equal to zero. In order to accomplish this correction, the processor typically applies a linear interpolation and a translation (herein, by way of example, an elevation) to the RIp values between adjacent end-experium points, setting both the beginning and end points equal to zero. The segments of a line 212 illustrate the line on which the interpolation is based, and a broken line 214 illustrates the translated, interpolated values of RIp, herein termed RIe values.

The interpolation described above relies on interpolation between two known end-experium points. In embodiments of the present invention, after a latest end-expirium point has been determined, the processor may estimate values of RIe at a time i, $\widehat{RIe}_i\, e_i$, until a next end-experium point is determined. The estimation typically performs a similar type of translation as that described above, from the latest determined end-expirium point.

The $\widehat{RIe}_i\, e_i$ values may be used to predict a provisional next end-expirium point, by comparing the $\widehat{RIe}_i\, e_i$ values with a user-defined threshold Th, i.e., by finding times when the condition $\widehat{RIe}_i\, e_i < Th$ is true. A typical value of Th is 2. Typically, the provisional next end-expirium point is assumed to be correct until an actual end-expirium point (a minimum value of RIp) is found. The actual end-expirium point then supersedes the provisional point.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. Apparatus for determining position and orientation coordinates of a probe within a body of a patient while compensating for respiration of the patient, the apparatus comprising:
   (i) a plurality of body-electrodes adapted for positioning in galvanic contact with a body of a patient;
   (ii) a probe having at least one conductive electrode and adapted for positioning in the body of the patient; and
   (iii) a control unit comprising:
      (a) an alternating current driver for measuring current between the at least one conductive electrode and the plurality of body-electrodes;
      (b) a voltage driver for measuring impedance between the at least one conductive electrode and the plurality of body-electrodes;
      (c) a processor, which is configured to:
         (i) track position and orientation coordinates of the probe during respiration of the patient using the at least one conductive electrode and the plurality of body-electrodes,
         (ii) determine respiration indications related to impedance measured between the body-electrodes during the respiration,
         (iii) calculate a function relating the tracked position and orientation coordinates of the probe to the respiration indications,
         (iv) apply the function to identify end-expirium points of the respiration of the patient based on subsequent indications related to the impedance and evaluating that the function is less than a predetermined threshold; and
         (v) determine respiratory compensated position and orientation coordinates of the probe using an estimate of respiratory movement of the probe based on the end-expirium points.

2. The apparatus according to claim 1, further comprising an electromagnetic coordinate sub-system, and wherein the processor is further configured to track the positions of the probe by determining the position and orientation coordinates of the probe using the electromagnetic coordinate sub-system.

3. The apparatus according to claim 1, wherein tracking the positions of the probe comprises computing the positions in response to currents between the at least one conductive electrode of the probe and the plurality of body-electrodes.

4. The apparatus according to claim 1, wherein the processor is further configured to determine the respiration indications by measuring respective currents between the at least one conductive electrode of the probe and the plurality of body-electrodes.

5. The apparatus according to claim 1, wherein the processor is further configured to calculate a function by formulating a matrix relating the impedances respiration indications related to impedances between the plurality of body-electrodes to the positions and orientation coordinates of the probe.

6. The apparatus according to claim 5, wherein the processor is further configured to formulate the matrix by determining a direction vector of respiration motion.

7. The apparatus according to claim 6, wherein the processor is further configured to determine the end-expirium points for the respiration motion in response to the matrix and the direction vector.

8. The apparatus according to claim 6, wherein the processor is configured to determine the end-experium points for the respiration based on a rate of change of the respiration indications, the matrix, and the direction vector.

9. An apparatus for determining position and orientation coordinates of a probe within a body of a patient while compensating for respiration of the patient, the apparatus comprising:
  (i) a plurality of body-electrodes adapted for positioning in galvanic contact with a body of a patient;
  (ii) a probe having at least one conductive electrode and adapted for positioning in the body of the patient; and
  (iii) a control unit comprising:
    (a) an alternating current driver for measuring current between the at least one conductive electrode and the plurality of body-electrodes;
    (b) a voltage driver for measuring impedance between the at least one conductive electrode and the plurality of body-electrodes;
    (c) a processor, which is configured to:
      (i) obtain position and orientation coordinates measurements of the probe using the at least one conductive electrode and the plurality of body-electrodes,
      (ii) track position and orientation coordinates of the probe during respiration of the patient based on the position and orientation coordinates measurements using the at least one conductive electrode and the plurality of body-electrodes,
      (iii) determine respiration indications related to impedances between the body-electrodes during respiration of the patient, the respiration indications being representative of a state of respiration of the patient,
      (iv) calculate a function relating the tracked position and orientation coordinates of the probe to the respiration indications,
      (v) apply the function to identify end-expirium points of the respiration based on subsequent respiration indications related to impedance measured between the at least one conductive electrode and the plurality of body-electrodes and evaluating that the function is less than a predetermined threshold,
      (vi) determine compensated position and orientation coordinates measurements of the probe using an estimate of the respiratory movement based on the end-expirium points, and
      (vii) determine respiratory compensated position and orientation coordinates of the probe based on the compensated position and orientation coordinates measurements of step (vi).

* * * * *